United States Patent
Büchel et al.

[11] 3,978,069
[45] Aug. 31, 1976

[54] PHENYL-IMIDAZOLYL-FATTY ACID DERIVATIVES

[75] Inventors: Karl Heinz Büchel; Werner Meiser; Manfred Plempel; Carl Metzger, Wuppertal-Elberfeld, Germany

[73] Assignee: Bayer Aktiengesellschaft, Germany

[22] Filed: Aug. 24, 1972

[21] Appl. No.: 283,327

Related U.S. Application Data

[62] Division of Ser. No. 38,531, May 18, 1970, Pat. No. 3,732,242.

[30] Foreign Application Priority Data

May 21, 1969 Germany............................ 1925994

[52] U.S. Cl. ..................... 260/293.7; 260/247.5 E; 260/309; 424/267
[51] Int. Cl.² ...................................... C07D 401/02
[58] Field of Search ............................... 260/293.7

*Primary Examiner*—Nicholas S. Rizzo
*Assistant Examiner*—Jose Tovar

[57] ABSTRACT

Phenyl-imidazolyl-fatty acid derivatives of the formula

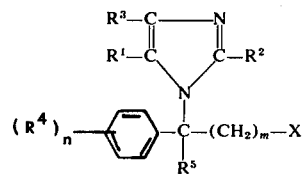

wherein
$R^1$, $R^2$, and $R^3$ are the same or different, and are hydrogen or lower alkyl;
$R^4$ is hydrogen, alkyl, lower alkoxy, alkylmercapto, or an electro negative moiety;
$R^5$ is benzene, benzene substituted by alkyl, lower alkoxy, alkylmercapto or an electro negative moiety, or $R^5$ is an aliphatic moiety;
X is a carboxyl moiety or a grouping of a functional carboxylic acid derivative;
$m$ is 0, 1, 2, 3, 4, 5 or 6; and
$n$ is 0, 1 or 2,
and pharmaceutically acceptable non-toxic salts thereof.

These phenyl-imidazolyl-fatty acid derivatives exhibit antimycotic activity.

2 Claims, No Drawings

PHENYL-IMIDAZOLYL-FATTY ACID DERIVATIVES

This is a division of application Ser. No. 38,531 filed May 18, 1970, now U.S. Pat. No. 3,732,242.

The present invention is concerned with phenyl-imidazolyl-fatty acid derivatives, salts thereof, and processes for their production. More particularly, the compounds of the present invention are phenyl-imidazolyl-fatty acid derivatives of the formula:

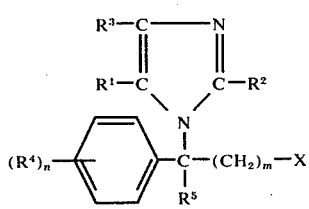

wherein
$R^1$, $R^2$ and $R^3$ are the same or different, and are hydrogen or lower alkyl;
$R^4$ is hydrogen, alkyl, lower alkoxy, lower alkylmercapto, or an electro negative moiety;
$R^5$ is benzene, benzene substituted by alkyl, lower alkoxy, lower alkylmercapto or an electro negative moiety, or $R^5$ is an aliphatic moiety;
X is a carboxyl moiety or a grouping of a functional carboxylic acid derivative;
m is 0, 1, 2, 3, 4, 5 or 6; and
n is 0, 1 or 2,
and pharmaceutically acceptable non-toxic salts thereof. These compounds are particularly useful for their antimycotic activity.

When any of the moieties $R^1$, $R^2$ or $R^3$ are alkyl, it is preferred that they contain 1 to 4 carbon atoms.

When $R^4$ is an alkyl moiety, it is preferred that it contain 1 to 4 carbon atoms, and methyl is particularly preferred. It is also preferred that the lower alkyl moieties and the lower alkylmercapto moieties contain 1 to 4 carbon atoms in the alkyl portion of the moieties. The term "alkyl" and "lower alkyl" as used herein is intended to embrace the straight as well as the branched chain alkyl moieties and includes, in addition to the alkyl moieties, the alkenyl and the alkynyl moieties as well.

Preferred electro negative substituents for $R^4$ are halogen, fluorine, chlorine, bromine or iodine, chlorine being particularly preferred, $NO_2$, trifluoromethyl and cyano, as well as $SO$-alkyl and $SO_2$-alkyl in which the alkyl moieties contain from 1 to 6 carbon atoms and preferably from 1 to 4 carbon atoms. As above indicated, these alkyl moieties may be straight or branched-chain and include, in addition to the alkyl groups, the alkenyl and alkynyl groups as well.

When $R^5$ is an aliphatic moiety, this can be straight or branched chain, saturated or unsaturated alkyl of 1 to 8 carbon atoms and preferably of 1 to 4 carbon atoms. The aliphatic moiety may be a saturated or unsaturated cycloaliphatic moiety of 3 to 6 carbon atoms and preferably of 5 to 6 carbon atoms in the ring system.

Examples of functional carboxylic acid derivatives for X include esters, carboxamide and nitrile groups.

If X is an ester moiety, its alcohol portion is a substituted, straight or branched chain, saturated or unsaturated aliphatic, cycloaliphatic or heteroaliphatic moiety. If this alcohol portion contains an alkyl group, this alkyl group is straight or branched chain of 1 to 18 carbon atoms and preferably of 1 to 12 carbon atoms, or such alkyl group substituted by an aromatic moiety.

If X is a carboxamide moiety, it is a free carboxamide moiety, a monoalkyl-carboxamide moiety or a dialkyl-carboxamide moiety wherein the alkyl portions are lower alkyl moieties, or lower alkyl moieties which may be linked to form a 5-, 6- or 7-membered ring system, or a 6-membered ring system having an oxygen, sulphur or nitrogen atom, or a 6-membered ring having an oxygen, sulphur or nitrogen atom which has attached thereto a lower alkyl moiety of 1 to 4 carbon atoms which is preferably in the p-position.

The salts of the present invention are physiologically compatible salts since the compounds of the present invention are intended for ministration to humans and animals. Thus, the salts may be formed with any of the known physiologically compatible acids, such as the hydrohalic acids, phosphoric acids, mono- and bifunctional carboxylic acids, hydroxycarboxylic acids, for example acetic acid, maleic acid, succinic acid, fumaric acid, tartaric acid, citric acid, salicylic acid, sorbic acid, lactic acid and 1,5-naphthalene-disulphonic acid.

The phenyl-imidazolyl-fatty acid derivatives of the present invention are produced by:

a. reacting a halogen derivative of the formula:

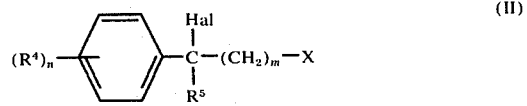

wherein
$R^4$, $R^5$, X, m, and n are as above defined, and
Hal is halogen, preferably chlorine,
with an imidazole or an alkyl-substituted imidazole in the presence of an acid-binding base or an excess of imidazole, expediently in an inert polar solvent, such as acetonitrile, toluene, xylene, chlorobenzene, cyclohexane, acetone, diethyl ketone, dimethyl formamide or dimethyl sulphoxide, at a temperature of from about 20°C. to about 180°C., and especially of from about 50°C. to about 100°C.;

b. reacting a halogen derivative of the formula:

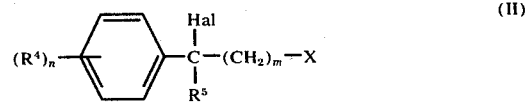

wherein
$R^4$, $R^5$, X, m and n are as above defined, and
Hal is halogen, preferably chlorine,
with an alkali metal or silver salt of imidazole or of an alkyl-substituted imidazole in an inert solvent, such as benzene, toluene, xylene or cyclohexane at a temperature of from about 20°C. to about 200°C., and preferably from about 50°C. to 120°C.; or c. reacting a hydroxy compound of the formula:

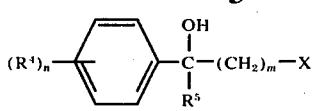

(III)

wherein

R⁴, R⁵, X, m and n are as above defined with imidazole or an alkyl-substituted imidazole, with the elimination of water.

These reactions can be carried out according to procedures which are per se known, for example they may be carried out in the melt or with the aid of the azeotropic elimination of water in the presence of higher-boiling solvents, such as xylene, chlorobenzene, etc., at the boiling point of the solvent used. In addition, it may be expedient at times to facilitate the elimination of water by the addition of a suitable dehydrating agent, such as alkaline earth metal oxide, for example MgO, BaO, CaO, or Al₂O₃.

The pharmaceutically acceptable non-toxic salts of the phenyl-imidazolyl-fatty acid derivatives are, of course, obtained by reacting the free base with the corresponding acid.

According to the present invention, a preferred group of compounds is represented by the formula:

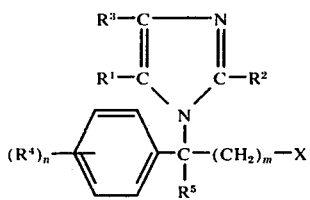

wherein
R¹ and R³ are both hydrogen;
R² is hydrogen or methyl;
R⁴ is hydrogen, methyl, methoxy, nitro, fluorine, chlorine, or bromine;
R⁵ is phenyl, phenyl-substituted in the p-position by fluorine, chlorine, bromine, methyl, methoxy or nitro, or R⁵ is a straight or branched chain alkyl moiety of 1 to 5 carbon atoms;
X is a carboxyl group, a moiety of the formula:

wherein R⁶ is straight or branched chain alkyl of 1 to 10 carbon atoms or benzyl, a moiety of the formula:

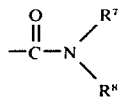

wherein
R⁷ and R⁸ are the same or different, and are hydrogen or methyl, or R⁷ and R⁸ together with the amide nitrogen form a morpholino or piperidino ring, or X is a cyano moiety;
m is 0, 1, 2, 3, 4, 5 or 6; and
n is 1.

Table I below lists representative phenyl-imidazolyl-fatty acid derivatives of the present invention.

TABLE I 1. diphenyl-imidazolyl-acetic acid methyl ester
2. diphenyl-imidazolyl-acetic acid
3. diphenyl-imidazolyl-acetic acid ethyl ester
4. diphenyl-imidazolyl-acetic acid n-propyl ester
5. diphenyl-imidazolyl-acetic acid isobutyl ester
6. diphenyl-imidazolyl-acetic acid n-octyl ester
7. diphenyl-imidazolyl-acetic acid n-decyl ester
8. diphenyl-imidazolyl-acetic acid benzyl ester
9. diphenyl-imidazolyl-acetic acid nitrile
10. phenyl-4-methylphenyl-imidazolyl-acetic acid methyl ester
11. phenyl-2-methylphenyl-imidazolyl-acetic acid methyl ester
12. β-imidazolyl-β,β-diphenyl propionic acid ethyl ester
13. hydrochloride of diphenyl-imidazolyl-acetic acid methyl ester
14. phenyl-4-chlorophenyl-imidazolyl-acetic acid ethyl ester
15. phenyl-4-chlorophenyl-imidazolyl-acetic acid methyl ester
16. phenyl-2-chlorophenyl-imidazolyl-acetic acid methyl ester
17. phenyl-isopropyl-imidazolyl-acetic acid ethyl ester
18. diphenyl-imidazolyl-acetic acid amide
19. diphenyl-imidazolyl-acetic acid methylamide
20. diphenyl-imidazolyl-acetic acid dimethylamide
21. diphenyl-imidazolyl-acetic acid morpholide
22. diphenyl-imidazolyl-acetic acid piperidide
23. bis-(4-chlorophenyl)-imidazolyl-acetic acid methyl ester
24. bis-(4-tolyl)-imidazolyl-acetic acid methyl ester.
25. bis-(4-bromophenyl)-imidazolyl-acetic acid methyl ester
26. bis-(4-fluorophenyl)-imidazolyl-acetic acid methyl ester and the hydrochloride salt thereof
27. bis-(4-methoxy-phenyl)imidazolyl-acetic acid methyl ester
28. bis-(4-nitro-phenyl)-imidazolyl-acetic acid ethyl ester hydrochloride
29. phenyl-isopropyl-imidazolyl-propionic acid ethyl ester
30. phenyl-isopentyl-imidazolyl-propionic acid ethyl ester
31. phenyl-ethyl-imidazolyl-isobutyric acid methyl ester
32. diphenyl-2-methyl-imidazolyl-acetic acid methyl ester
33. phenyl-tert.-butyl-imidazolyl-acetic acid methyl ester
34. diphenyl-imidazolyl-acetic acid methyl ester-tartrate
35. diphenyl-imidazolyl-acetic acid methyl ester-succinate
36. diphenyl-imidazolyl-acetic acid methyl ester sulphate
37. diphenyl-imidazolyl-acetic acid methyl ester-methane-sulphonate
38. diphenyl-imidazolyl-acetic acid methyl ester-naphthalene-1,5-disulphonate.

Particularly preferred compounds according to the present invention are diphenyl-imidazolyl-acetic acid methyl ester and the hydrochloride salt thereof.

The starting materials required for the preparation of the compounds of the present invention are per se known or are obtainable according to processes which themselves are known per se.

The following non-limitative examples more particularly point out and illustrate the present invention.

EXAMPLE 1

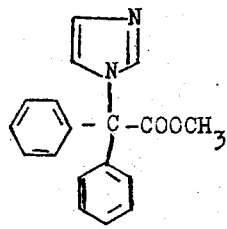

(1)

13 g (0.05 mole) diphenyl-chloroacetic acid methyl ester (b.p. 140°C/0.1 mm Hg, prepared from diphenyl-chloroacetic acid chloride and methanol according to Ber. 22, 1537) are heated with 10 g imidazole in 100 ml acetonitrile at boiling temperature for 18 hours. After distilling off the solvent in a vacuum, 50 ml of water are added and the mixture is extracted with methylene chloride. After drying over sodium sulphate, the solvent is distilled off in a vacuum and the residue recrystallized from a little ethyl acetate. The diphenyl-imidazolyl-acetic acid methyl ester is thus obtained in the form of colourless crystals of m.p. 155°C (with decomposition).

EXAMPLE 2

The corresponding carboxylic acid i.e. diphenyl-imidazolyl-acetic acid is obtained by hydrolysis of the diphenyl-imidazolyl-acetic acid methyl ester obtained in Example 1, with an alcoholic potassium hydroxide solution.

EXAMPLES 3–8

The compounds of these Examples were obtained according to the procedure set forth in Example 1, by reacting imidazole with the following reactants:

From 13.7 g diphenyl-chloroacetic acid ethyl ester (0.05 mole) (Ber. 22, 1537): the diphenyl-imidazolyl-acetic acid ethyl ester of m.p. 104°C.

From 14.4 g diphenyl-chloroacetic acid propyl ester (b.p. 155°C./0.3 mm Hg): the diphenyl-imidazolyl-acetic acid n-propyl ester of m.p. 71°C.

From 15.1 g diphenyl-chloroacetic acid isobutyl ester (b.p. 150°C./0.2 mm Hg): the diphenyl-imidazolyl-acetic acid isobutyl ester as oil.

From 16.0 g diphenyl-chloroacetic acid octyl ester (b.p. 195°C./0.3 mm Hg): the diphenyl-imidazolyl-acetic acid n-octyl ester as oil.

From 19.3 g diphenyl-chloroacetic acid decyl ester: the diphenyl-imidazolyl-acetic acid n-decyl ester of m.p. 48°C.

From 16.8 g diphenyl-chloroacetic acid benzyl ester: the diphenyl-imidazolyl-acetic acid benzyl ester as oil.

EXAMPLE 9

5.9 g diphenyl-chloroacetonitrile (prepared from diphenyl-chloroacetamide, Ber. 41, 3593 by heating in phosphorus oxychloride; b.p. 130°C./0.4 mm Hg) are heated with 5 g imidazole in 50 ml acetonitrile at boiling temperature for 18 hours. After treating with 20 ml of water, the mixture is extracted with methylene chloride. The solvent is distilled off after drying in a vacuum. The solid residue is recrystallized from ethyl acetate/petroleum ether. Diphenyl-imidazolyl-acetonitrile i.e. diphenyl-imidazolyl-acetic acid nitrile of m.p. 98°C. is thus obtained.

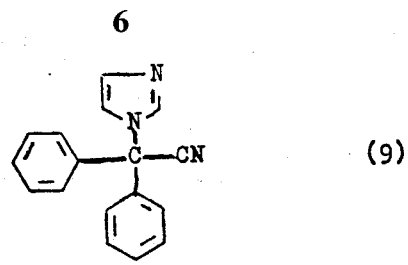

(9)

EXAMPLE 10

13.7 g phenyl-p-tolyl-chloroacetic acid methyl ester (prepared from p-tolyl-magnesium bromide and benzoyl-formic acid methyl ester and treatment with $PCl_5$; (b.p. 150°C./0.3 mm Hg) are heated with 10 g imidazole in 100 ml acetonitrile at boiling temperature for 16 hours. The acetonitrile is distilled off in a vacuum. The residue is treated with 50 ml of water and then extracted with methylene chloride. The methylene chloride solution is distilled off in a vacuum and the residue recrystallized from a little ethyl acetate. The phenyl-p-tolyl-imidazolyl-acetic acid methyl ester i.e. phenyl-4-methylphenyl-imidazolyl-acetic acid methyl ester of m.p. 146°C. is thus obtained.

EXAMPLE 11

The phenyl-o-tolyl-imidazolyl-acetic acid methyl ester i.e. phenyl-2-methylphenyl-imidazolyl-acetic acid methyl ester (m.p. 148°C.) is obtained in an analogous way from phenyl-o-tolyl-chloroacetic acid methyl ester (b.p. 160°C./0.4 mm Hg).

EXAMPLE 12

14.4 g (0.05 mole) β-chloro-β,β-diphenyl-propionic acid ethyl ester (prepared from β-hydroxy-β,β-diphenyl-propionic acid ethyl ester, Ber. 40, 4538, by treatment with phosphorus pentachloride) are heated in 100 ml acetonitrile with 10 g imidazole at boiling temperature for 16 hours. The solvent is distilled off in a vacuum, the residue treated with 50 ml of water and extracted with methylene chloride. After drying, the solvent is distilled off in a vacuum. The β-imidazolyl-β,β-diphenyl-propionic acid ethyl ester is thus obtained in the form of crystals of m.p. 75° C.

EXAMPLE 13

5 g of the diphenyl-imidazolyl-acetic acid methyl ester of Example 1 are dissolved in carbon tetrachloride and hydrogen chloride is introduced with cooling. The carbon tetrachloride is decanted off from the precipitated oily salt and the salt is reprecipitated from acetone/ether. The hydrochloride of the above base i.e. diphenyl-imidazolyl-acetic acid methyl ester hydrochloride is thus obtained; m.p. 131°C. (decomp.).

EXAMPLE 14

15.45 g (0.05 mole) phenyl-p-chlorophenyl-chloroacetic acid ethyl ester (prepared from p-chlorophenyl-magnesium bromide and benzoyl-formic acid ethyl ester and subsequent treatment with thionyl chloride: b.p. 160°C./0.2 mm Hg) are boiled with 10 g imidazole in 100 ml acetonitrile for 16 hours. After distilling off the solvent, 50 ml of water are added, and the mixture is extracted with methylene chloride. After drying, the solvent is distilled off in a vacuum and the phenyl-p-chlorophenyl-imidazolyl-acetate acid ethyl ester i.e. phenyl-4-chlorophenyl-imidazolyl-acetic acid ethyl ester is obtained in the form of an oil which solidifies after a fairly long time.

EXAMPLE 15

The phenyl-p-chlorophenyl-imidazolyl-acetic acid methyl ester i.e. phenyl-4-chlorophenyl-imidazolyl-acetic acid methyl ester of melting point 135°C. (ethyl acetate) is obtained in an analogous way by reacting phenyl-p-chlorophenyl-chloroacetic acid methyl ester and imidazole.

EXAMPLE 16

The phenyl-o-chlorophenyl-imidazolyl-acetic acid methyl ester i.e. phenyl-2-chlorophenyl-imidazolyl-acetic acid methyl ester of melting point 138°C. (ethyl acetate) is obtained by the method described in Example 14 by reacting phenyl-o-chlorophenyl-chloroacetic acid methyl ester and imidazole.

EXAMPLE 17

12 g (0.05 mole) phenyl-isopropyl-chloracetic acid ethyl ester (b.p. 95°C./0.3 mm Hg) are heated with 10 g imidazole and 100 ml acetonitrile at boiling temperature for 18 hours. After distilling off the solvent in a vacuum, 50 ml of water are added and the mixture is extracted by shaking with methylene chloride. The methylene chloride is dried and distilled off in a vacuum. The phenyl-isopropyl-imidazolyl-acetic acid ethyl ester is thus obtained in the form of an oil.

EXAMPLE 18

12.27 g (0.05 mole) diphenyl-chloroacetic acid amide (Ber. 41, 3593) are heated with 11.8 g imidazole in 100 ml acetonitrile at boiling temperature for 18 hours. After cooling, the crystals are suspended in water and rinsed. After recrystallization from methanol, diphenyl-imidazolyl-acetic acid amide of m.p. 218°C. is obtained.

EXAMPLE 19

13 g (0.05 mole) diphenyl-chloroacetic acid methylamide (prepared from diphenyl-chloroacetic acid chloride and methylamine in analogy with Ber. 41, 3593; m.p. 108°C) are heated with 11.5 g imidazole in 100 ml acetonitrile at boiling temperature for 18 hours. After cooling, the crystals are filtered off with suction, digested with water and rinsed. After recrystallization from methanol, diphenyl-imidazolyl-acetic acid methylamide of b.p. 237°C is obtained.

EXAMPLE 20

18.1 g diphenyl-chloroacetic acid dimethylamide (m.p. 128°C, prepared by analogy with Example 19) are heated with 15.6 g imidazole in 120 ml acetonitrile at boiling temperature for 18 hours. The solvent is distilled off in a vacuum. After the addition of 70 ml of water, the mixture is extracted with methylene chloride. After drying, the solvent is distilled off in a vacuum and the solid residue is recrystallized from methanol. The diphenyl-imidazolyl-acetic acid dimethyl amide of m.p. 202°C is thus obtained in the form of colourless crystals.

EXAMPLE 21

The diphenyl-imidazolyl-acetic acid morpholide is obtained from 15.5 g diphenyl-chloroacetic acid morpholide (m.p. 113°C) and 11 g imidazole in 100 ml acetonitrile on analogy with Example 20.

The hydrochloride of diphenyl-imidazolyl-acetic acid morpholide of m.p. 118°C is obtained by adding ethereal hydrochloric acid to a solution of diphenyl-imidazolyl-acetic acid morpholide in ethyl acetate.

EXAMPLE 22

The diphenyl-imidazolyl-acetic acid piperidide of m.p. 160°C is obtained from 15.4 g diphenyl-chloracetic acid piperidide (m.p. 82°C) and 10 g imidazole in 100 ml acetonitrile in analogy with Example 20.

EXAMPLE 23

162.6 g (0.434 mole) of 4,4'-dichlorodiphenyl-bromoacetic acid methyl ester (prepared from 4,4'-dichlorobenzilic acid methyl ester) and phosphorus pentabromide (b.p. 190°/0.5 mm Hg) are heated to the boil for 14 hours, with stirring, with 90 g (1.32 moles) of imidazole in 1 liter of acetonitrile. The acetonitrile is distilled off in a vacuum. For the removal of imidazole, the residue is twice shaken with, in each case, 1.3 liters of water, then taken up in 950 ml of methylene chloride and again extracted with 1.8 liters of water. After drying with sodium sulphate, the methylene chloride is distilled in a vacuum. The residue is boiled out four times with, in each case, 250 ml of ether; the ethereal solution, after clarification with charcoal, is precipitated with ethereal hydrochloric acid. The precipitate is digested with absolute ether and taken up in methylene chloride; after filtration, ethyl acetate is added. When the methylene chloride is evaporated on a water-bath, the hydrochloride of bis-(4-chlorophenyl)-imidazolyl-acetic acid methyl ester of the melting point 150°C (with decomposition) crystallizes out in colourless crystals.

When the hydrochloride is shaken with methylene chloride and solution of sodium carbonate, a solution of the base is obtained. After this has been dried, distillation in a vacuum is effected and the residue is recrystallized from dry ether. These are so obtained the colourless crystals of bis-(4-chlorophenyl)-imidazolyl-acetic acid methyl ester of the melting point 132°C.

EXAMPLE 24

Analogously with Example 23, there is obtained from 13.3 g 4,4-ditolyl-$\alpha$-bromoacetic acid methyl ester and 10 g imidazole in 100 ml acetonitrile the hydrochloride of bis-(4-tolyl)-imidazolyl-acetic acid methyl ester of the melting point 140°C (with decomposition) in colourless crystals.

EXAMPLE 25

19.4 g 4,4'-dibromodiphenylbromoacetic acid methyl ester (prepared from 4,4'-dibromodiphenylacetic acid methyl ester and bromosuccinimide) are heated to the boil for 15 hours with 8.4 g imidazole in 8.5 ml acetonitrile. The acetonitrile is distilled off in a vacuum. The residue is shaken twice with, in each instance, 110 ml of water and decanted. The residue is then taken up in about 100 ml of methylene chloride and again extracted with 80 ml of water. After drying of the methylene chloride, the latter is distilled off in a vacuum. The residue is boiled out four times with, in each case, 100 ml of absolute ether. The ether is clarified with charcoal and precipitation is effected with ethereal hydrochloric acid. The hydrochloride precipitating in lumps is digested twice with absolute ether, then taken up in methylene chloride. After filtration, ethyl acetate is added, and the methylene chloride is evaporated on a water-bath. After cooling, the hydrochloride of bis-(4-bromophenyl)-imidazolyl-acetic acid methyl ester of the melting point 140°C crystallizes out in colourless crystals.

The hydrochloride is shaken with methylene chloride and solution of sodium carbonate. The solution of the base in methylene chloride is dried and distilled off in a vacuum. The residue is recrystallized from a little absolute ether. There are so obtained the colourless crystals of bis-(4-bromophenyl)-imidazolyl-acetic acid methyl ester of the melting point 135°C.

EXAMPLE 26

In the same manner as in Example 23, there is obtained from 40.1 g 4,4′difluorodiphenylbromoacetic acid methyl ester (b.p. 143°/0.4 mm Hg, prepared from 4,4′-difluorodiphenylacetic acid methyl ester and N-bromosuccinimide) and 23.6 g imidazole in 236 ml acetonitrile the hydrochloride of bis-(4-fluorophenyl)-imidazolyl-acetic acid methyl ester of the melting point 147°C. From this there is obtained, with solution of sodium carbonate in methylene chloride, the free base of the melting point 128°C.

EXAMPLE 27

In the same manner as in Example 23, there is obtained from 4,4′-dimethoxybenzilic acid methyl ester (m.p. 110°C) with phosphorus pentachloride via 4,4′-dimethoxyphenyl-α-chloroacetic acid methyl ester with imidazole in acetonitrile the bis-(4-methoxyphenyl)-imidazolyl-acetic acid methyl ester of the melting point 131°C.

EXAMPLE 28

In the same manner as in Example 23, with analogous working up, there is obtained from 10.25 g 4,4′-dinitrodiphenylbromoacetic acid ethyl ester (m.p. 130°C., prepared from 4,4′-dinitrodiphenylacetic acid ethyl ester and N-bromosuccinimide) and 5 g imidazole in 70 ml acetonitrile the hydrochloride of bis-(4-nitrophenyl)-imidazolyl-acetic acid ethyl ester of the melting point 130°C. (with decomposition) in colourless crystals.

EXAMPLE 29

Analogously with Example 12, by reacting chlorophenyl-isopropyl-propionic acid ethyl ester and imidazole,phenyl-isopropyl-imidazolyl-propionic acid ethyl ester is obtained as oil, and from this there is obtained, with ethereal hydrochloric acid, the hydrochloride of the melting point 194°C.

EXAMPLE 30

Analogously with Example 12, by reacting chlorophenyl-isopentyl-propionic acid ethyl ester and imidazole, phenyl-isopentyl-imidazolyl-propionic acid ethyl ester is obtained as oil.

EXAMPLE 31

Analogously with Example 12, by reacting chlorophenyl-ethyl-isobutyric acid ethyl ester and imidazole, phenyl-ethyl-imidazolyl-isobutyric acid ethyl ester is obtained as oil.

EXAMPLE 32

13 g diphenyl-α-chloroacetic acid methyl ester (0.05 mole) are heated to the boil for 20 hours with 12.1 g 2-methyl-imidazole in 100 ml acetonitrile. The acetonitrile is distilled off in a vacuum. 200 ml of water are added to the residue, which is then taken up in 200 ml methylene chloride. The methylene chloride is extracted twice with, in each case, 150 ml of water, dried and distilled off in a vacuum. The residue is recrystallized from a little ethyl acetate. There is so obtained the diphenyl-2-methyl-imidazolyl-acetic acid methyl ester of the melting point 136°C.

EXAMPLE 33

12.7 g (0.05 mole) phenyl-tert.-butyl-chloroacetic acid methyl ester (b.p. 96°C./0.3 mm Hg) are heated to the boil for 17 hours with 10 g imidazole and 100 ml acetonitrile. After the solvent has been distilled off in a vacuum, treatment with 70 ml of water is effected followed by extraction with methylene chloride. The methylene chloride is again extracted with 30 ml of water, dried and distilled off in a vacuum. There is so obtained the phenyl-tert.-butyl-imidazolyl-acetic acid methyl ester as oil, which solidifies after a long time.

EXAMPLE 34

From the diphenyl-imidazolyl-acetic acid methyl ester obtainable according to Example 1 and the appropriate acid listed, the following salts of diphenyl-imidazolyl-acetic acid methyl ester are obtained:

| Acid | Salt | Melting Point | |
|---|---|---|---|
| Tartaric | Tartrate | 135°C. | (decomp.) |
| Succinic | Succinate | 107°C. | '' |
| Sulphuric | Sulphate | 145°C. | '' |
| Methane-sulphonic | Methane-sulphonate | 154°C. | '' |
| Naphthalene-1,5-disulphonic | Naphthalene-1,5-disulphonate | 229°C. | '' |

The antimycotic activity of the phenyl-imidazolyl-fatty acid derivatives and the pharmaceutically acceptable non-toxic salts thereof is shown by the in-vitro and in-vivo data set forth below. Tables II and III illustrate the in-vitro activity of these compounds which is primarily fungistatic. Fungicidal effects with a reduction of the inoculum by 95% in 24 hours can be achieved with a two- to three-fold minimum inhibitory concentration.

The determination of the minimum inhibition concentrations stated in Tables II and III in γ/ml of nutrient solution was effected.

a. in the case of dermatophytes and mould fungi, in Sabouraud's milieu d'epreuve,
b. in the case of yeasts, in yeast/meat broth bouillon.

The incubation temperature was 28°C. and the duration of incubation was 48 to 96 hours.

TABLE II

| Compound from Example | Trichophyton ment. without Serum | Trichophyton ment. with Serum | Candida albicans without Serum | Candida albicans with Serum | Pen. comune | Aspergillus niger without Serum | Aspergillus niger with Serum | Microsp. felineum |
|---|---|---|---|---|---|---|---|---|
| 1 | <4 | <4 | 4 | 100 | <4 | <4 | <4 | <4 |
| 3 | <4 | <4 | 10 | 40 | <4 | <4 | <4 | <4 |
| 4 | <4 | <4 | 4 | 20 | <4 | <4 | <4 | <4 |
| 5 | <4 | <4 | 4 | <100 | 10 | 10 | 40 | <4 |
| 6 | <4 | 40 | 20 | <100 | >100 | 4 | 100 | 20 |
| 7 | 10 | | 10 | | >100 | | | |
| 9 | <4 | <4 | 20 | 100 | <4 | <4 | <4 | <4 |
| 10 | 10 | | 10 | | 10 | | | |
| 11 | 10 | | 10 | | 10 | | | |
| 14 | <4 | <4 | 4 | >100 | <4 | <4 | 4 | <4 |
| 17 | 4 | | 10 | | — | | | |
| 18 | >100 | | >100 | | >100 | | | |
| 19 | 100 | 100 | >100 | | >100 | | | |
| 20 | 20 | 20 | >100 | | >100 | | | |

Minimum inhibition concentration in γ/ml test medium in the case of

TABLE III

Minimum inhibition concentration in γ/ml nutrient medium

| Compound from Example | Trichophyton mentagrophytes Serum with | Trichophyton mentagrophytes Serum without | Candida albicans Serum with | Candida albicans Serum without | Penicillium comune | Aspergillus niger Serum with | Aspergillus niger Serum without | Microsporon felineum | Hystoplasma capsulatum | Coccidiodes immitis |
|---|---|---|---|---|---|---|---|---|---|---|
| 12 | 4 | — | 20 | — | — | — | — | — | — | — |
| 13 | <1 | <1 | <1 | <1 | 1 | 4 | 4 | 1 | <1 | <1 |
| 21 (Hydrochloride) | 40 | 40 | 100 | 100 | >100 | — | — | — | — | — |
| 23 (Base) | <4 | 10 | 4 | >100 | 10 | 10 | 100 | <4 | — | — |
| 23 (Hydrochloride) | <4 | 20 | 10 | 10 | 20 | 4 | 100 | 10 | — | — |
| 25 (Base) | <4 | 40 | <4 | 10 | >100 | >100 | — | 10 | — | — |
| 25 (Hydrochloride) | <4 | 100 | <4 | 40 | 40 | >100 | — | 10 | — | — |
| 26 | <4 | <4 | 10 | 20 | 10 | 4 | 4 | 100 | — | — |
| 27 | 4 | — | 10 | — | — | — | — | — | — | — |
| 28 | 100 | 100 | 4 | 40 | >100 | — | — | — | — | — |
| 29 (Base) | 40 | — | >100 | — | — | — | — | — | — | — |
| 29 (Hydrochloride) | 10 | — | 100 | — | — | — | — | — | — | — |
| 30 | 10 | — | 1 | — | — | — | — | — | — | — |
| 31 | 4 | — | 100 | — | — | — | — | — | — | — |
| 32 | >100 | — | >100 | — | — | — | — | — | — | — |

The following compounds representative of those of the present invention were tested for in-vivo activity according to the procedures set forth below:

| | |
|---|---|
| diphenyl-imidazolyl-acetic acid methyl ester | (Example 1) |
| diphenyl-imidazolyl-acetic acid ethyl ester | (Example 3) |
| diphenyl-imidazolyl-acetic acid n-propyl ester | (Example 4) |
| diphenyl-imidazolyl-acetic acid iso-butyl ester | (Example 5) |
| phenyl-2-methylphenyl-imidazolyl-acetic acid methyl ester | (Example 11) |
| diphenyl-imidazolyl-acetic acid methyl ester hydrochloride | (Example 13) |
| diphenyl-imidazolyl-acetic acid morpholide hydrochloride | (Example 21) |
| bis-(4-chlorophenyl)-imidazolyl-acetic acid methyl ester | (Example 23) |
| bis-(4-chlorophenyl)-imidazolyl-acetic acid methyl ester hydrochloride | (Example 23) |
| bis-(4-bromophenyl)-imidazolyl-acetic acid methyl ester (base) | (Example 25) |
| bis-(4-bromophenyl)-imidazolyl-acetic acid methyl ester hydrochloride | (Example 25) |
| bis-(4-fluorophenyl-imidazolyl-acetic acid methyl ester hydrochloride | (Example 26) |
| bis-(4-methoxyphenyl)-imidazolyl-acetic acid methyl ester (base) | (Example 27) |
| bis-(4-nitrophenyl)-imidazolyl-acetic acid ethyl ester hydrochloride | (Example 28) |

A. Oral treatment of experimental candidiasis of the white mouse with the compounds of Examples 1, 3, 4, 5, 11, 13, 21, 23, 25, 26, 27 and 28.

Male mice of the strain $CF_1$ — SPF of 20–22 g weight were infected intravenously with 2–5 × $10^6$ Candida albicans cells per mouse. With this experimental arrangement, untreated animals died of the infection within 6 days.

When 30–60 mg of these compounds per kilogram body weight of the infected animals was administered orally once or twice daily, an average of 13 to 16 of the 20 animals receiving the administration survived on the 6th day after infection. In the case of treatment with the compound of Example 13, 19 to 20 of the animals of the group of 20 survived. The optimum dosage for the compounds of Examples 1, 3, 5, 13, 23 and 28 was shown to be 50 mg/kg twice daily. The optimum dosage for compounds of Examples 4, 11, 21, 25, 26 and 27 was shown to be 60 mg/kg twice daily.

For oral application, the preparations were suspended in 0.25%-strength glucose-agar and administered with the oesophageal sound.

B. Parenteral treatment of experimental candidiasis and histoplasmosis of the mouse with the compound from Example 13.

In the case of a parenteral administration of the compound from Example 13 in a dosage of 25 mg/kg twice daily, 18 of 20 animals survived 6 days after the infection.

C. Local treatment of experimental guinea-pig trichophytosis with the compound from Example 13.

Infection of the animals was effected by Trichophyton mentagrophytes. From the 3rd day after infection, the infection point was treated once daily by application of 0.5 ml of a 1%-strength solution of the active compound in polyethyleneglycol 400. This treatment was continued up to the 14th day after infection. Within the therapy period, the dermatosis healed up. In the case of untreated infected control animals, bleeding ulcerations of the infection point as well as loss of hair occured up to about 30 days after infection.

The phenyl-imidazolyl-fatty acid derivatives and the pharmaceutically acceptable non-toxic salts thereof are thus particularly useful in treating the following diseases:

a. in human medicine:
1. Dermatomycoses caused by fungi of the species Trichophytes, Microsporium, Epidermophytes, Aspergillus, Candida albicans and other yeasts,
2. Organomycoses caused by yeasts, mould fungi and Dermatophytes, b. in veterinaymedicine:
Dermatomycoses and organomycoses by yeasts, mould fungi and Dermatophytes.

The compounds of the present invention may be administered orally, parenterally or topically.

While in general it has proved advantageous to administer from about 20 mg/kg to about 50 mg/kg per day in order to achieve satisfactory results, it is to be appreciated that it may be necessary to deviate from these ranges and that a variety of factors such as the body weight of the test animal or patient, the method of administration, the animal species, the past medical history of the patient, the individual reaction to the medication, the type of formulation, and the moment in time or the time interval at which it is to be administered are all among the factors which are to be taken into consideration. It may in certain cases be sufficient to use less than the above indicated minimum amount, whereas in other cases it may be necessary to administer more than the above indicated amount. If larger amounts are to be administered, it is preferred that these be administered in several dosages during the course of the day.

Also according to the present invention are pharmaceutical compositions which comprise the phenyl-imidazolyl-fatty acid derivatives or the pharmaceutically acceptable non-toxic salts thereof in combination with pharmaceutically acceptable non-toxic carriers and diluents. Suitable forms of application, in combination with various inert carriers, are the following: tablets, capsules, powders, sprays, agueous suspensions, injectable solutions, elixirs, syrups and the like. Such carriers comprise solid diluents or fillers, a sterile aqueous medium as well as non-toxic organic solvents and the like. Tablets and the like intended for oral application may, of course, be provided with sweetening additives and similar substances. In the aforesaid case the therapeutically active compound should be present at a concentration of about 0.5 to 90 percent by weight of the total mixture, i.e. in quantities which are sufficient to achieve the range of dosage mentioned above.

The pharmaceutical compositions according to the present invention may include a protective envelope containing the active compound and if the compound is in combination with a diluent or carrier, the envelope may contain said diluent or carrier as well.

The term "medicament in dosage unit form" as used in the present specification means a medicament as defined above in the form of discrete portions each containing a unit dose, or a multiple or sub-multiple of a unit dose of the active compound or compounds. Such portions may, for example, be in monolithic coherent form, such as tablets, suppositories, pills or dragees; in wrapped or concealed form, such as wrapped powders, cachets, sachets, or capsules; in ampoules, either free or as a sterile solution suitable for parenteral injection; or in any other form known to the art.

In the case of oral application, the tablets can obviously also contain additives, such as sodium citrate, calcium carbonate and dicalcium phosphate together with various other additives, such as starch, preferably potato starch, and the like, and binding agents, such as polyvinyl-pyrrolidone, gelatin and the like. Lubricants, such as magnesium stearate, sodium lauryl sulphate and talc may also be added for the production of tablets. In the case of aqueous suspensions and/or elixirs which are intended for oral application, the active substances may be used with various flavouring agents, colouring substances, emulsifiers and/or together with diluents, such as water, ethanol, propylene glycol, glycerol and similar compounds or combinations of this type.

In the case of parenteral application, solutions of the active substances in sesame or peanut oil, or in aqueous propylene glycol or N,N-dimethyl formamide can be used as can sterile aqueous solutions in the case of water-soluble compounds. Aqueous solutions of this kind should be buffered in usual manner if necessary; furthermore, the liquid diluent should previously be rendered isotonic by the addition of the necessary amount of salt or glucose. Such aqueous solutions are particularly suitable for intravenous, intramuscular, intraperitoneal and subcutaneous injections. Sterile aqueous media of this kind are prepared in known manner.

Local application is effected in the form of 0.5 – 5%, preferably 1%, solutions (for example in dimethyl formamide, glycerol, water; alcohol, such as ethanol and isopropanol and buffer solutions), but also as emulsions, suspensions, powders and tablets.

When the compounds of the present invention are administered, they may of course be administered either in the form of a free base or in the form of a pharmaceutically acceptable non-toxic salt thereof. Thus, the free base and the salts may be contained in capsules, tablets, pastilles, dragees and ampoules, and the like for oral administration which is a particularly facile mode of administration.

The phenyl-imidazolyl-fatty acid derivatives and the pharmaceutically acceptable non-toxic salts thereof, or the pharmaceutical compositions above described may be formulated in unit dosage form wherein each dosage unit is so formulated that it provides a single dose of the active compound, or it may contain a plurality of doses, or a fraction of a dose. Common dosages include two, three or four doses or a half, quarter or third of a dose.

While hitherto known antimycotics are effective only against yeasts, such as amphotericin B, or only against zygomycetes, such as griseofulvin, the compounds of the present invention even upon oral administration are effective against yeast as well as against zygomycetes. In particular, the compounds of the present invention exhibit substantially less toxicity than amphotericin B and their effectiveness is substantially greater than that of griseofulvin.

In addition to their antimycotic activity, the compounds of the present invention also exhibit activity against pathogenic protozoa, such as trypanosomes, trichomonades, Entamoeba histolytica, causative organisms of malaria, as well as an activity against gram-positive cocci, such as staphylococci, and against gram-negative bacteria, such as E.coli. When the compounds of the present invention are administered to humans or animals for such activity, they are administered in the same general manner and amounts as known compounds exhibiting those activities.

What is claimed is:

1. A compound selected from the group consisting of a phenyl-imidazolyl carboxylic acid derivative of the formula:

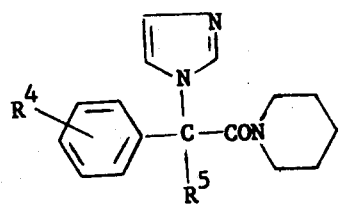

wherein
R$^4$ is hydrogen, alkyl of 1 to 4 carbon atoms, alkoxy of 1 to 4 carbon atoms, alkylmercapto of 1 to 4 carbon atoms, chloro, fluoro, bromo or nitro; and
R$^5$ is alkyl of 1 to 8 carbon atoms, phenyl or phenyl substituted by alkyl of 1 to 4 carbon atoms, alkoxy of 1 to 4 carbon atoms, alkylmercapto of 1 to 4 carbon atoms, chloro, fluoro, bromo or nitro, and the pharmaceutically acceptable nontoxic salts thereof.

2. The compound which is diphenyl-imidazolyl-acetic acid piperidide.

* * * * *